United States Patent
Peng (10) Patent No.: US 11,207,468 B2
(45) Date of Patent: Dec. 28, 2021

(54) SYRINGE

(71) Applicant: Yu-Fan Lin, Taoyuan (TW)

(72) Inventor: Chiung-Hsien Peng, Taoyuan (TW)

(73) Assignee: Yu-Fan Lin, Taoyuan (TW)

( * ) Notice: Subject to any disclaimer, the term of this patent is extended or adjusted under 35 U.S.C. 154(b) by 129 days.

(21) Appl. No.: 16/605,331

(22) PCT Filed: Apr. 17, 2018

(86) PCT No.: PCT/CN2018/083331
§ 371 (c)(1),
(2) Date: Oct. 15, 2019

(87) PCT Pub. No.: WO2018/196653
PCT Pub. Date: Nov. 1, 2018

(65) Prior Publication Data
US 2020/0268984 A1  Aug. 27, 2020

(30) Foreign Application Priority Data

Apr. 25, 2017 (CN) .......................... 201710273874.8

(51) Int. Cl.
*A61M 5/32* (2006.01)
*A61M 5/315* (2006.01)
*A61M 5/34* (2006.01)

(52) U.S. Cl.
CPC ...... *A61M 5/3216* (2013.01); *A61M 5/31515* (2013.01); *A61M 5/3221* (2013.01); *A61M 5/3269* (2013.01); *A61M 5/348* (2013.01); *A61M 2005/3231* (2013.01)

(58) Field of Classification Search
CPC .................. A61M 5/322; A61M 5/345; A61M 2005/323; A61M 2005/3235; A61M 2005/3239
See application file for complete search history.

(56) References Cited

U.S. PATENT DOCUMENTS

| 5,370,619 A | * | 12/1994 | Rossi | ..................... A61M 5/322 |
| | | | | 604/110 |
| 2006/0084915 A1 | * | 4/2006 | Chang | ................... A61M 5/322 |
| | | | | 604/110 |

FOREIGN PATENT DOCUMENTS

| CN | 2635108 Y | 8/2004 |
| CN | 2724733 Y | 9/2005 |
| CN | 2764414 Y | 3/2006 |
| CN | 204133964 U | 2/2015 |
| CN | 205031663 U | 2/2016 |

* cited by examiner

*Primary Examiner* — Laura A Bouchelle
(74) *Attorney, Agent, or Firm* — Muncy, Geissler, Olds & Lowe, P.C.

(57) ABSTRACT

A syringe is provided, including a syringe barrel, a needle set and a push rod. A front end part is provided in the syringe barrel. An end of the needle set has an open area, the open area is transversely provided with a first snap part. The push rod is slidably disposed within the syringe barrel, and an end of the push rod facing the front end part has a second snap part. When the push rod is slidingly moved to the front end part, the second snap part is engaged with the first snap part.

10 Claims, 8 Drawing Sheets

SYRINGE

BACKGROUND OF THE INVENTION

Field of the Invention

The present invention relates to a syringe.

Description of the Prior Art

After performing an injection operation, fingers of an operator may be accidentally hurt by a needle of a used syringe when covering the used syringe with a protecting cap, which may results in infection of diseases. Therefore, the syringe disclosed in TWM488998, for example, includes a push rod having a hooked arm, when the push rod is moved toward an adapter of the syringe for injection, the hooked arm of the push rod is inserted within the adapter and engaged with an engaging groove disposed within the adapter so as to withdraw a needle set of the syringe into the syringe barrel for safety.

However, the syringe as disclosed above has the following disadvantages. During engagement of the hooked arm and the engaging groove, the hooked arm axially pushes the adapter since an opening of the engaging groove is smaller than a diametric dimension of the hooked arm, which means that the needle set is moved axially; and then a hook of the hooked arm is deformed and engaged with the engaging groove. Therefore, the needle of the needle set is moved or shaken during injection, which results in discomfort during injection and blood stasis of injection site.

The present invention is, therefore, arisen to obviate or at least mitigate the above-mentioned disadvantages.

SUMMARY OF THE INVENTION

The main object of the present invention is to provide a syringe which can reduce discomfort during injection and avoid blood stasis of injection site.

To achieve the above and other objects, the present invention provides a syringe, including a syringe barrel, a needle set and a push rod. The syringe barrel has a receiving portion and a front end part disposed therein. The needle set includes a needle, and the needle set is detachably assembled to the front end part. An end of the needle set remote from the needle has an open area, and the open area has a first snap part transversely disposed thereon. The first snap part is disposed between at least one first position and at least one second position circumferentially on an inner wall of the open area. The push rod is slidably disposed within the receiving portion, and an end of the push rod facing the front end part has a second snap part which is engageable with the first snap part.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Please refer to FIGS. 1 to 6 for a preferable embodiment of the present invention. A syringe of the present invention includes a syringe barrel 1, a needle set 2 and a push rod 5.

The syringe barrel 1 has a receiving portion 11 and a front end part 12 disposed therein.

The needle set 2 includes a needle 4, and the needle set 2 is detachably assembled to the front end part 12. An end of the needle set 2 remote from the needle 4 has an open area 31, and the open area 31 has a first snap part 32 transversely disposed thereon. The first snap part 32 is disposed between at least one first position 21 and at least one second position 22 circumferentially on an inner wall of the open area 31.

The push rod 5 is slidably disposed within the receiving portion 11, and an end of the push rod 5 facing the front end part 12 has a second snap part 52 which is engageable with the first snap part 32.

Preferably, the needle set 2 further includes an adapter 3, and the adapter 3 is detachably assembled to the front end part 12. The needle 4 is disposed on an end of the adapter 3 remote from the syringe barrel 1, and an end of the adapter 3 remote from the needle 4 has the open area 31. The first snap part 32 divides the open area 31 into a first spacing portion 311 and a second spacing portion 312 which are located radially by the first snap part 32, and the second snap part 52 penetrates into the adapter 3 from one of the first spacing portion 311 and the second spacing portion 312. The needle 4 includes a needle base 41 and a needle body 42 which are connected with each other, and an end of the needle base 41 remote from the needle body 42 has a flange 43 which is screwed to the adapter 3 for easy assembling or disassembling.

Figures 7, 8:
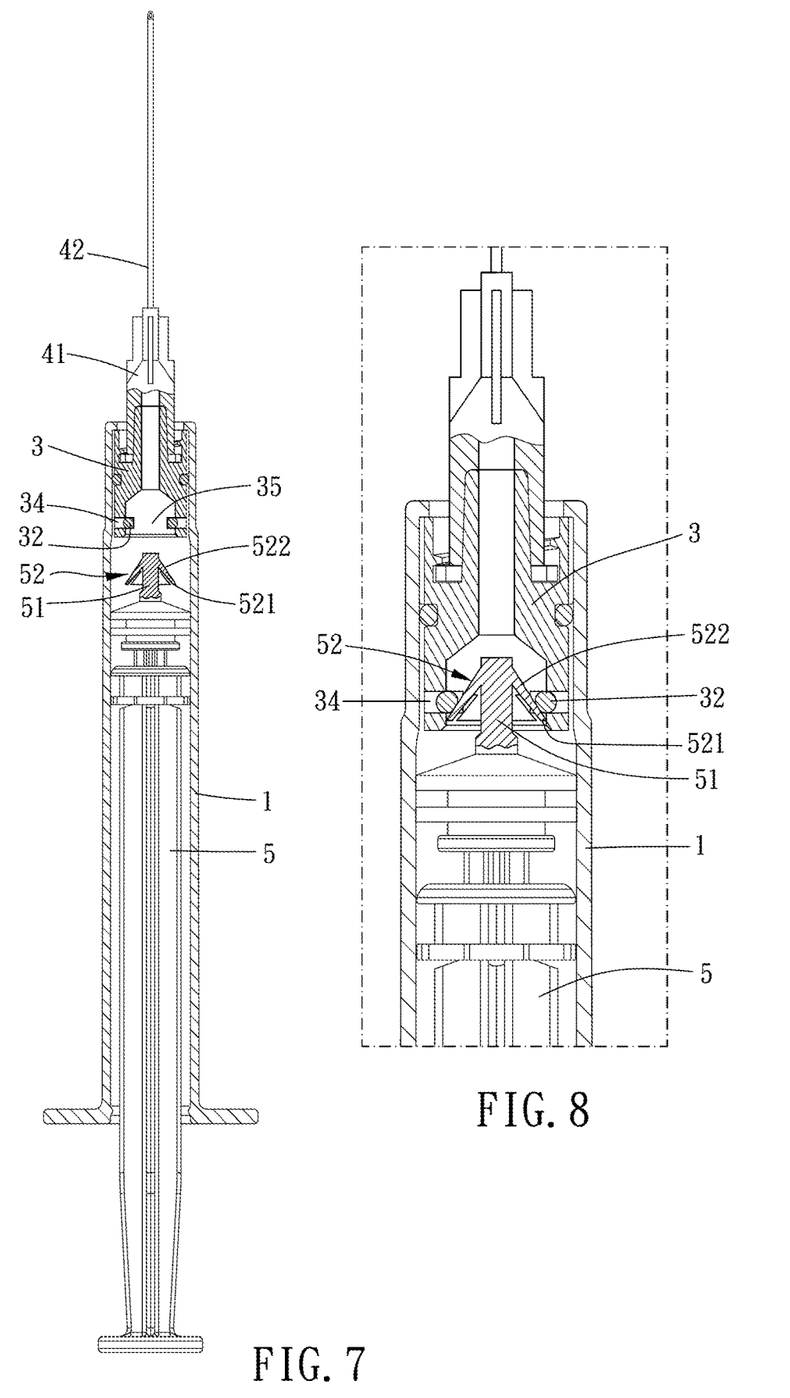
FIGS. 7 to 11 are schematic diagrams of a preferable embodiment of the present invention in operation.
Figure 9:
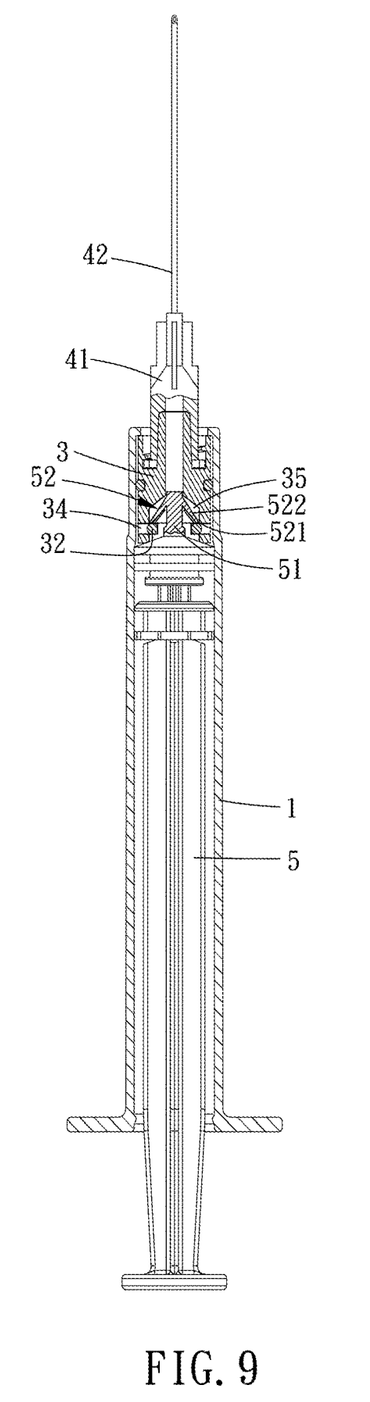
Figure 10:
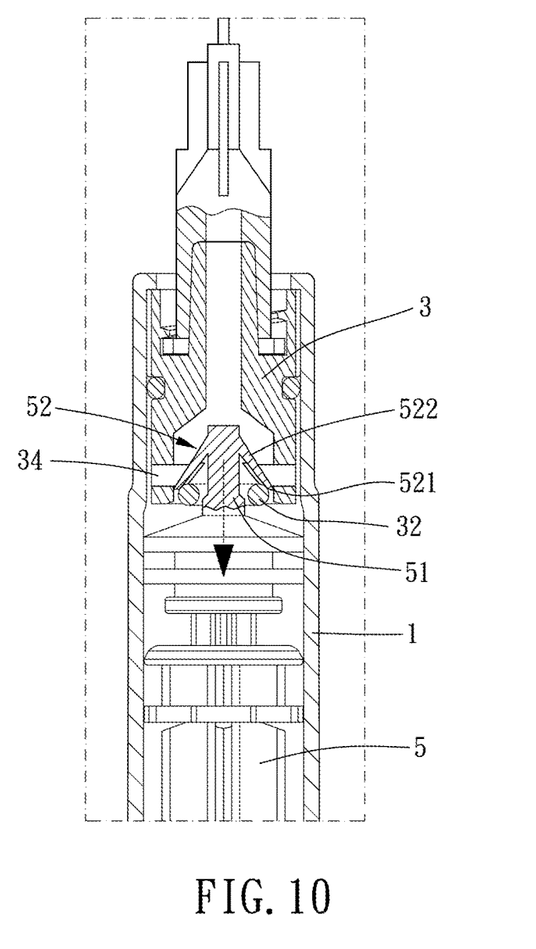
Figure 11:
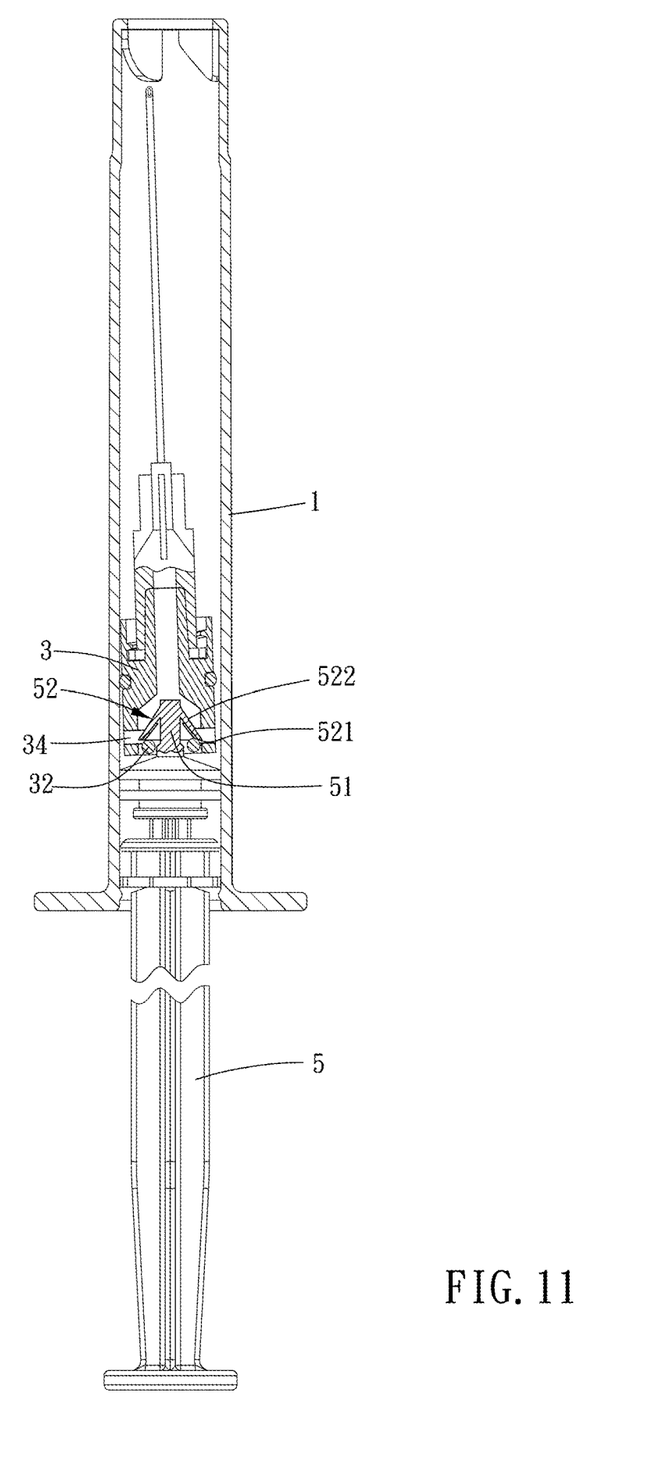

Please refer to FIGS. 7 to 11, when the push rod 5 is moved toward the front end part 12, the second snap part 52 radially urges the first snap part 32 to deform and slips over the first snap part 32 (as shown in FIG. 8). The second snap part 52 penetrates into the needle set 2 from one of the first spacing portion 311 and the second spacing portion 312, and the second snap part 52 is blockably engaged with the first snap part 32 (as shown in FIGS. 9 and 10) and the needle set 2 is withdrawable into the receiving portion 11 by the push rod 5 (as shown in FIG. 11) so that the needle set 2 is not exposed out of the syringe barrel 1 to avoid unexpected poke.

Figure 1:
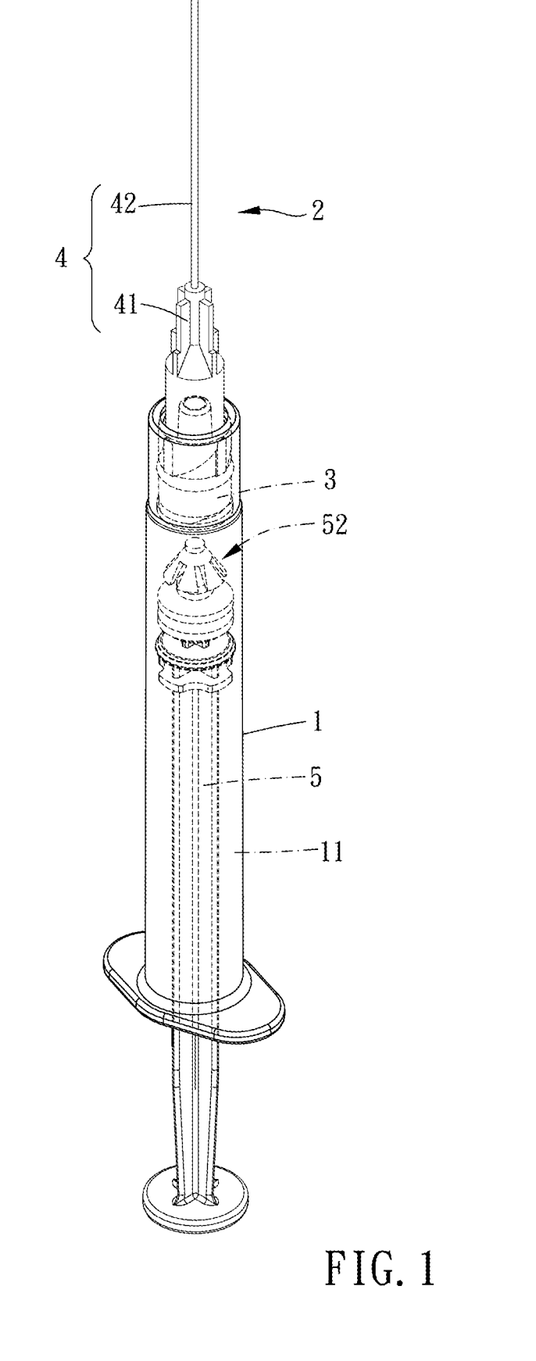
FIG. 1 is a stereogram of a preferable embodiment of the present invention.
Figure 2:
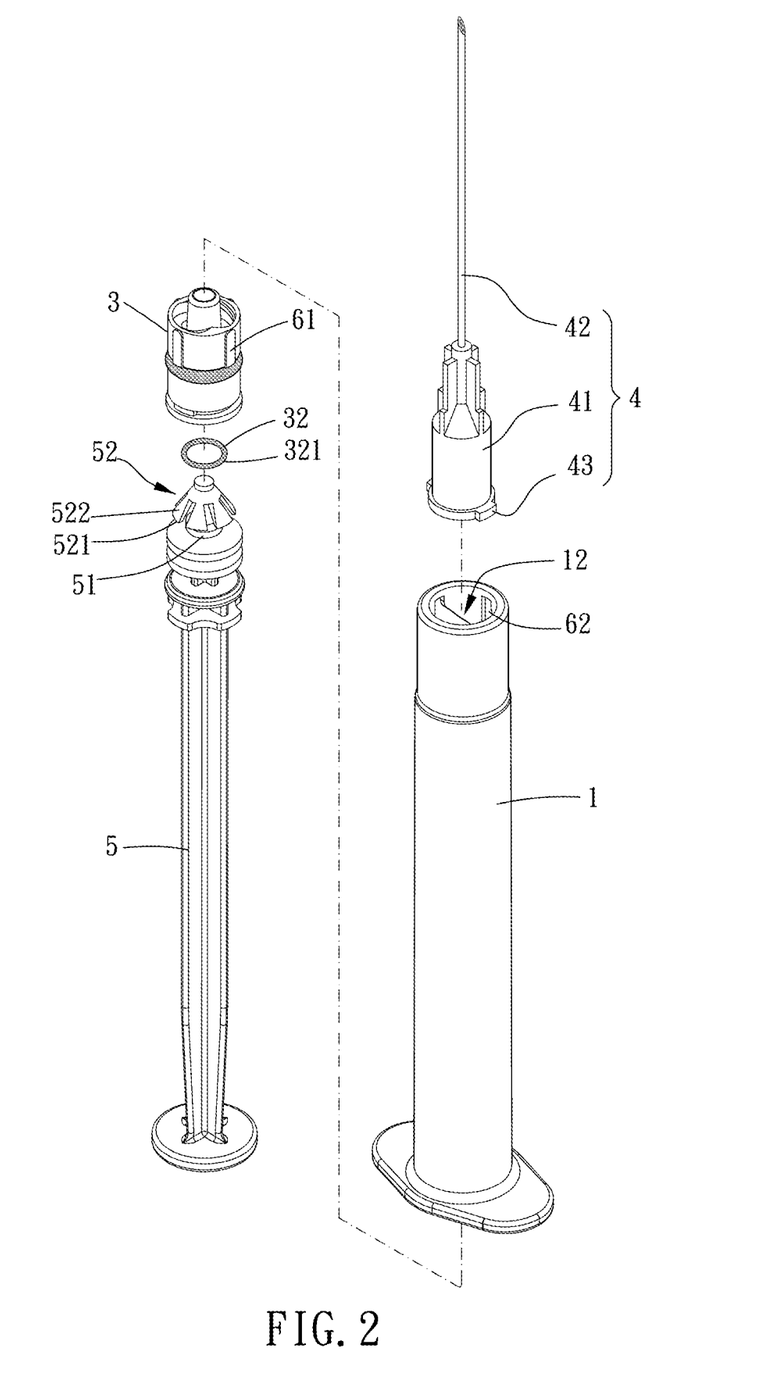
FIG. 2 is a breakdown drawing of a preferable embodiment of the present invention.
Figure 3:
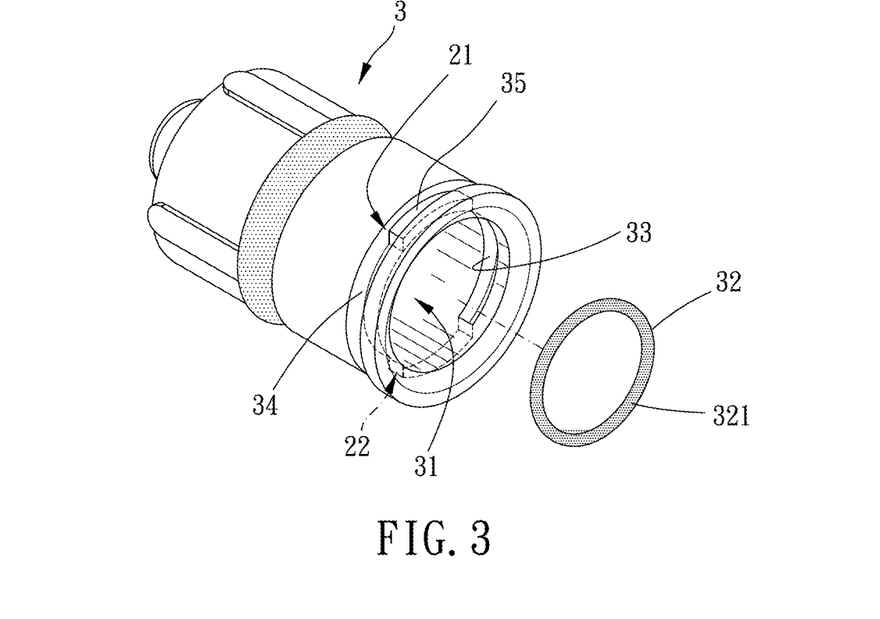
FIG. 3 is a partial breakdown drawing of a preferable embodiment of the present invention.
Figure 4:
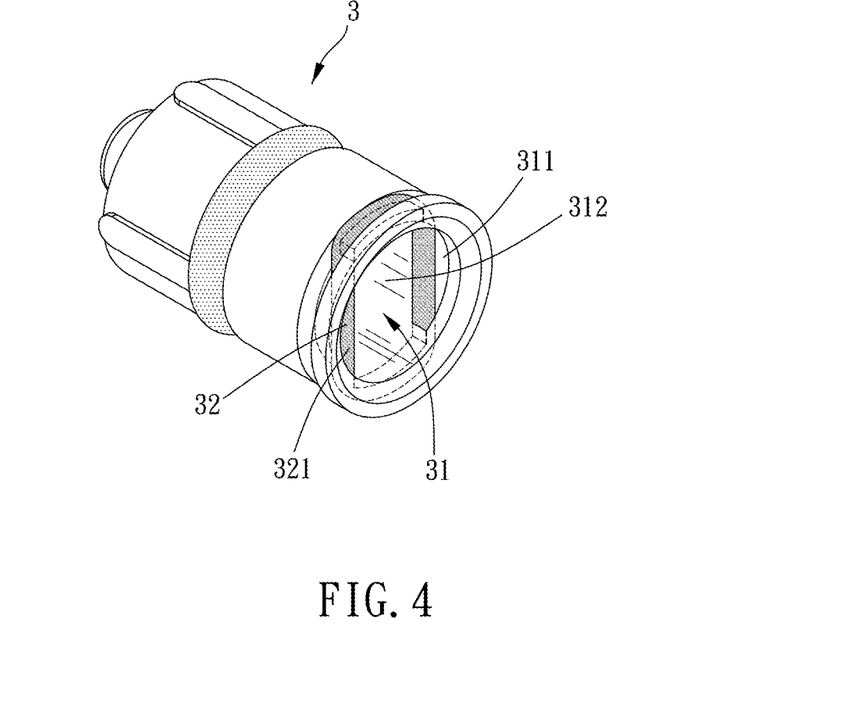
FIG. 4 is a partial stereogram of a preferable embodiment of the present invention.
Figure 5:
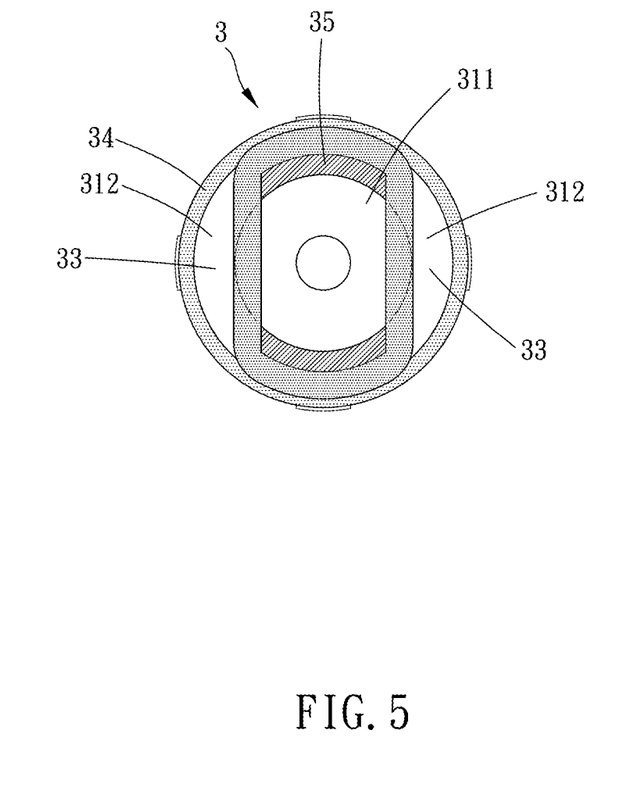
FIG. 5 is a partial side view of a preferable embodiment of the present invention.
Figure 6:
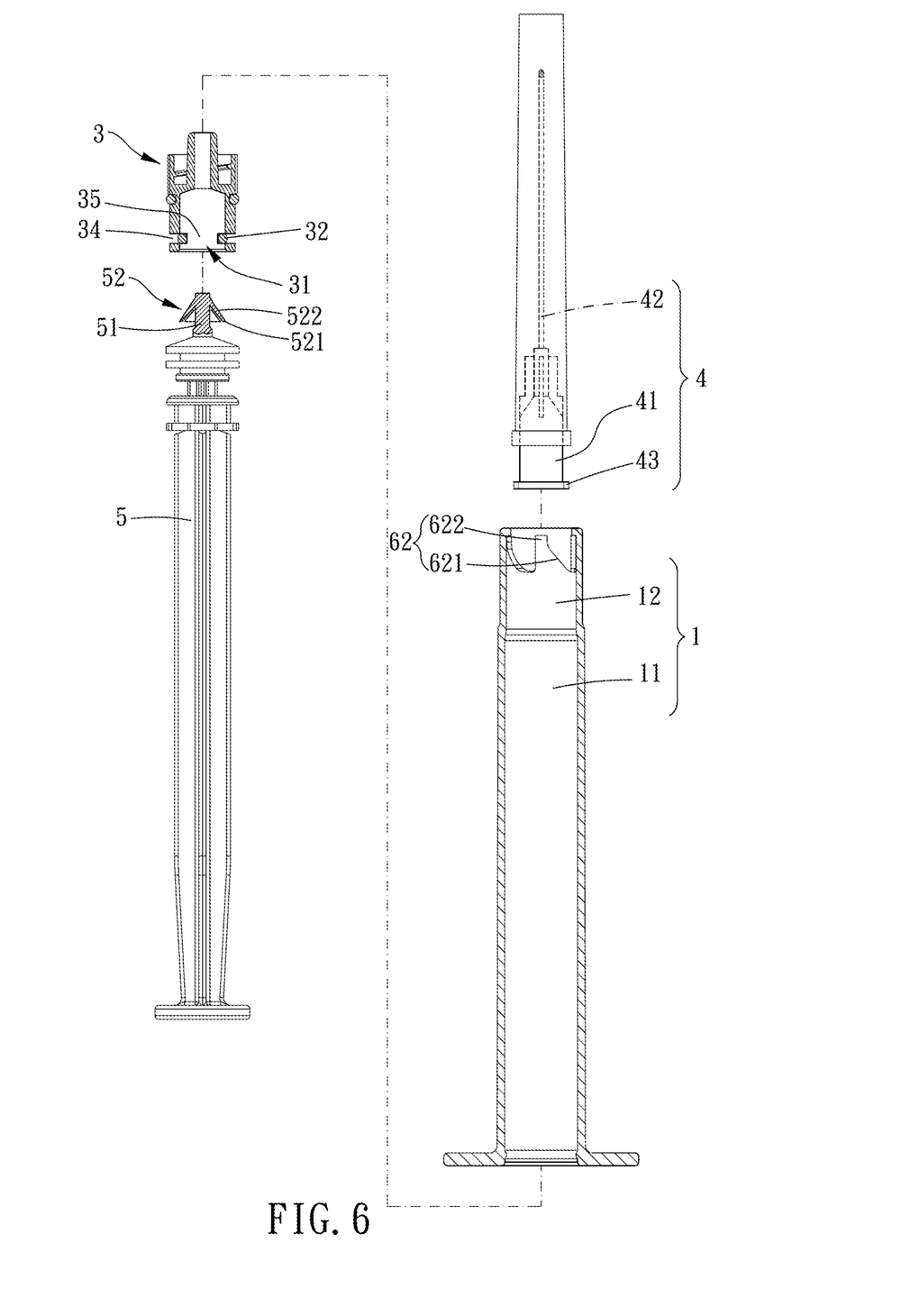
FIG. 6 is a cross-sectional schematic diagram of a preferable embodiment of the present invention.

Specifically, a wall of the adapter 3 has at least one slot 33 disposed radially therethrough and communicated with an interior of the adapter 3, and the first snap part 32 is embedded within the at least one slot 33 and disposed across the open area 31. In this embodiment, the wall of the adapter 3 has two said slots 33, and the two said slots 33 are located at two radially opposite sides of the wall of the adapter 3. The first snap part 32 is an elastic ring 321 (as shown in FIG. 3), and the elastic ring 321 is sleeved to the adapter 3 and embedded within the two said slots 33. The elastic ring 321 is transversely disposed at the open area 31 and within the two said slots 33, and the elastic ring 321 has advantages of easy assembling and disassembling and low cost. The elastic ring 321 divides the open area 31 into one said first spacing portion 311 and two said second spacing portions 312 located at two opposite sides of the said first spacing portion 311. Preferably, an end of the push rod 5 facing the front end part 12 has a column 51, and the column 51 has the second snap part 52. The first snap part 32 is non-passed through a center of the open area 31, a radial cross-sectional area of the first spacing portion 311 is larger than a radial cross-sectional area of the second spacing portion 312, and the column 51 penetrates into the adapter 3 from the first spacing portion 311. Therefore, the second snap part 52 of the column 51 can effectively radially urge the first snap part 32 to deform, which considerably reduces force applied by the column 51 in an axial direction of the adapter 3 and prevents the adapter 3 from shaking axially so as to reduce discomfort during injection and avoid blood stasis of injection site.

Moreover, an outer wall of the adapter 3 has an annular groove 34 disposed thereon, the annular groove 34 is communicated with the two said slots 33, and the elastic ring 321 is received within the annular groove 34 so as to avoid sliding of the elastic ring 321 relative to the adapter 3.

In this embodiment, the adapter 3 further includes two blocking portions 35. Each of the two blocking portions 35 is disposed between two opposite ends of each of the two said slots 33, and the elastic ring 321 is abutted against the two blocking portions 35.

Specifically, the second snap part 52 has at least one hooked portion 521, and each of the at least one hooked portion has an inclined section 522 outwardly tilted to the axial direction of the adapter 3. At least one of the inclined section 522 urges and deforms the first snap part 32 in a radial direction of the adapter 3, and when the at least one hooked portion 521 slips over the first snap part 32, at least one of the at least one hooked portion 521 is blockably engaged with the first snap part 32. In this embodiment, the second snap part 52 has a plurality of said hooked portions 521, and when the push rod 5 is rotated relative to the syringe barrel 1, the first snap part 32 slips off respective of said inclined sections 522 and is engaged with at least one of the plurality of said hooked portions 521. Therefore, the first snap part 32 and the second snap part 52 are blockably engaged with each other without excessively pushing the push rod 5 toward the needle 4, which prevents the adapter 3 from shaking axially and reduces discomfort during injection.

One of the outer wall of the adapter 3 and an inner wall of the front end part 12 has at least one rib 61, and the other of the outer wall of the adapter 3 and the inner wall of the front end part 12 has at least one guiding groove 62. Each of the at least one guiding groove 62 has a guiding inclined surface 621 and a recession 622. In this embodiment, the outer wall of the adapter 3 has a plurality of said ribs 61, and the inner wall of the front end part 12 has a plurality of said guiding grooves 62. Each of the plurality of said ribs 61 is inserted within respective one of said recession 622. When the adapter 3 is assembling to the front end part 12, said guiding inclined surfaces 621 guide the plurality of said ribs 61, and the adapter 3 is rotated and each of the plurality of said ribs 61 is inserted within respective one of said recession 622 so that the adapter 3 is received within the front end part 12 in tight-fit.

In summary, the second snap part radially urges the first snap part to deform, which considerably reduces force applied by the column in the axial direction of the adapter and prevents the adapter from shaking axially so as to reduce discomfort during injection and avoid blood stasis of injection site.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A syringe, including:
   a syringe barrel, having a receiving portion and a front end part which are disposed therein;
   a needle set, including a needle, the needle set being detachably assembled to the front end part, an end of the needle set remote from the needle having an open area, the open area having a first snap part transversely disposed thereon, the first snap part being disposed between at least one first position and at least one second position which are located circumferentially on an inner wall of the open area;
   a push rod, slidably disposed within the receiving portion, an end of the push rod facing the front end part having a second snap part which is engageable with the first snap part;
   wherein when the push rod is moved toward the front end part, the second snap part radially urges the first snap part and slips over the first snap part and into the needle set; wherein at least a portion of the first snap part extends linearly in a direction from the at least one first position toward the at least one second position, and the first snap part is axially positioned on the inner wall of the open area before and after urging by the second snap part.

2. The syringe of claim 1, wherein the first snap part divides the open area into a first spacing portion and a second spacing portion which are located radially by the first snap part, the second snap part penetrates into the needle set from one of the first spacing portion and the second spacing portion, the second snap part is blockably engaged with the first snap part and the needle set is withdrawable into the receiving portion by the push rod.

3. The syringe of claim 1, wherein the needle set further includes an adapter, the adapter is detachably assembled to the front end part, the needle is disposed on an end of the adapter remote from the syringe barrel, and an end of the adapter remote from the needle has the open area.

4. The syringe of claim 3, wherein a wall of the adapter has at least one slot disposed radially therethrough and communicated with an interior of the adapter, and the first snap part is embedded within the at least one slot and disposed across the open area.

5. The syringe of claim 4, wherein the wall of the adapter has two said slots, the two said slots are located at two radially opposite sides of the wall of the adapter, the first snap part is an elastic ring, and the elastic ring is sleeved to the adapter and embedded within the two said slots.

6. The syringe of claim 5, wherein an outer wall of the adapter has an annular groove disposed thereon, the annular groove is communicated with the two said slots, and the elastic ring is received within the annular groove.

7. The syringe of claim 5, wherein the adapter further includes two blocking portions, each of the two blocking portions is disposed between two opposite ends of the two said slots, and the elastic ring is abutted against the two blocking portions.

8. The syringe of claim 3, wherein the second snap part has at least one hooked portion, each of the at least one hooked portion has an inclined section outwardly tilted to an axial direction of the adapter, at least one of the inclined section urges and deforms the first snap part in a radial direction of the adapter, and when the at least one hooked portion slips over the first snap part, at least one of the at least one hooked portion is blockably engaged with the first snap part.

9. The syringe of claim 8, wherein the second snap part has a plurality of said hooked portions, and when the push rod is rotated relative to the syringe barrel, the first snap part slips off respective of said inclined sections and is engaged with at least one of the plurality of said hooked portions.

10. The syringe of claim 3, wherein an end of the push rod facing the front end part has a column, the column has the second snap part disposed thereon, the first snap part is non-passed through a center of the open area, the needle includes a needle base and a needle body which are connected with each other, an end of the needle base remote from the needle body has a flange which is screwed to the adapter.

* * * * *